United States Patent [19]

Handschuh

[11] 4,210,557
[45] Jul. 1, 1980

[54] NON-HIGH DENSITY LIPOPROTEIN PRECIPITANT

[75] Inventor: Gerald J. Handschuh, Carlsbad, Calif.

[73] Assignee: Beckman Instruments, Inc., Fullerton, Calif.

[21] Appl. No.: 970,050

[22] Filed: Dec. 15, 1978

[51] Int. Cl.$^2$ .................... G01N 31/02; G01N 33/16; G09K 3/00

[52] U.S. Cl. ................................. 252/408; 23/230 B; 210/51; 210/52; 210/54; 424/2; 424/3

[58] Field of Search .................... 195/99, 103.5 R; 252/408; 23/23 DB; 424/2, 3; 210/51, 52, 54

[56] References Cited

U.S. PATENT DOCUMENTS

| | | | |
|---|---|---|---|
| 3,395,210 | 7/1968 | Lenahan et al. | 195/103.5 R |
| 3,816,262 | 6/1974 | Monte et al. | 252/408 |
| 3,880,714 | 4/1975 | Babson | 195/99 |
| 3,955,925 | 5/1976 | Proksch et al. | 252/408 |
| 3,960,492 | 6/1976 | Di Giulio | 252/408 |
| 3,996,162 | 12/1976 | McCall | 252/408 |
| 4,014,744 | 3/1977 | Chang | 195/103.5 R |
| 4,039,285 | 8/1977 | Teipel | 252/408 |
| 4,045,176 | 8/1977 | Proksch et al. | 252/408 |
| 4,056,468 | 11/1977 | Breiter et al. | 23/230 B |
| 4,147,606 | 4/1979 | Colias | 424/12 |
| 4,158,544 | 6/1979 | Louderback | 252/408 |

*Primary Examiner*—Teddy S. Gron
*Attorney, Agent, or Firm*—Robert J. Steinmeyer; John E. Vanderburgh; Robert S. Frieman

[57] ABSTRACT

A reagent, of the type comprising a precipitator capable of precipitating low density lipoproteins, very low density lipoproteins, and other non-high density lipoproteins, is improved by the addition thereto of a non-interfering suitable agent capable of enhancing the flocculation of a precipitant formed by the precipitator and the various non-high density lipoprotein fractions in highly lipemic serum.

34 Claims, 2 Drawing Figures

NON-HIGH DENSITY LIPOPROTEIN PRECIPITANT

BACKGROUND OF THE INVENTION

1. Field of the Invention

This invention relates to a reagent for selectively precipitating low density lipoproteins, very low density lipoproteins and other non-high density lipoproteins in serum.

2. Description of the Prior Art

Considerable attention has been given to the determination of cholesterol in the high-density lipoprotein (HDL) fraction of human serum. In 1951, Barr et al[1] published the results of a study indicating a definite relationship between levels of HDL and the occurrence of coronary heart disease. Since then, further research[2,3,4] has provided strong evidence of a negative correlation between HDL-cholesterol levels and the risk of coronary heart disease in both men and women over the age of 50. In particular, the well-documented epidemiologic data from the National Institute of Health (NIH)-sponsored studies,[5,6,7] have established an inverse correlation between decreased levels of HDL-cholesterol and premature heart disease. Studies done in other countries have supported these conclusions.[8,9]

Determination of HDL-cholesterol has, until recently, been a difficult assay to perform. For many years, ultracentrifugation was the only acceptable means of separating the various lipoprotein fractions of human serum.[10] The high cost of the equipment and the time required for this type of analysis have severely restricted the application of this methodology in the clinical laboratory. Electrophoresis on various support media[11] offered a simpler approach for the separation of lipoprotein fractions but did not permit ready quantitation of the lipids in the separated fractions. More recently a number of simpler methods have been developed for the isolation of plasma HDL by selective precipitation of the other lipoprotein fractions[12,13,14,15]. The Lipid Research Clinic (LRC) of the NIH has evaluated these procedures and proposed a standardized method in which cholesterol is measured colorimetrically (modified Lieberman-Burchard technique) in the HDL fraction obtained after precipitation of low-density lipoproteins (LDL) and very low density lipoproteins (VLDL) from whole serum with heparin/manganese.[16]

Although extensively used today, this method represents serious problems in terms of its routine use in the clinical laboratory. Heparin preparations vary considerably from one manufacturer to another and even from lot to lot. Thus the laboratory using this procedure must verify the completeness of LDL and VLDL precipitations each time a different lot of heparin is used. The Lieberman-Burchard procedure has major drawbacks in the area of specificity and accuracy and requires the use of corrosive and noxious chemicals. To improve the specificity and avoid the use of dangerous chemicals, the heparin/manganese precipitation proposed by LRC has been coupled with the enzymatic determination of cholesterol in the HDL supernatant thus obtained. This combination has presented special problems of its own, such as formation of a visible precipitate with the enzymatic reagent and falsely increased cholesterol values.[17]

A method employing dextran sulfate and magnesium to precipitate LDL, VLDL, and other non-HDL from whole serum or plasma has been shown to precipitate quantitatively all the VLDL and LDL in human serum and to yield accurate and reproducible values for HDL cholesterol in combination with the enzymatic cholesterol procedure.[18] These precipitated LDL, VLDL, and other non-HDL fractions are removed by centrifugation. The cholesterol in the HDL remaining in the supernatant is quantitated by means of the following enzyme reactions.

Cholesterol Esters $\xrightarrow{CE^*}$ Cholesterol + Fatty Acids

Cholesterol + $O_2$ $\xrightarrow{CO^{**}}$ Cholesten-3-one + $H_2O_2$

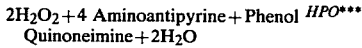
$2H_2O_2$ + 4 Aminoantipyrine + Phenol $\xrightarrow{HPO^{***}}$ Quinoneimine + $2H_2O$

*CE = cholesterol esterase
**Cholesterol oxidase
***HPO = Peroxidase

The quinoneimine produced has an absorbance maximum at 500 nm. The intensity of the color produced is directly proportional to the concentration of cholesterol in the HDL fraction.

With very lipemic serum it is very difficult to perform the above mentioned centrifugation step required to remove the precipitated LDL, VLDL, and other non-HDL fractions from the supernatant. Therefore, in the case of very lipemic serum, it is necessary to either dilute the serum prior to the precipitation step or filter the supernatant subsequent to the centrifugation step to avoid falsely elevated HDL cholesterol values.

It would be very advantageous if one could avoid having to perform these additional steps required to circumvent the problem posed when very lipemic serum is assayed for HDL cholesterol.

It is an object of the instant invention to provide a non-HDL precipitant which can be employed without the necessity of having to perform either of the two auxiliary steps previously found necessary in order to obtain accurate HDL cholesterol values when assaying very lipemic serum.

The object of the instant invention is accomplished by adding a suitable inert, insoluble, adsorbtive composition to a reagent comprising a precipitator capable of precipitating LDL, VLDL, and other non-HDL fractions.

SUMMARY OF THE INVENTION

This invention encompasses a reagent of the type comprising a precipitator capable of precipitating LDL, VLDL, and other non-HDL fractions. The reagent of this invention is characterized in that it further comprises a non-interfering suitable agent capable of enhancing the flocculation of a precipitant formed by the precipitator and the various non-HDL fractions in highly lipemic serum.

Many precipitants capable of precipitating LDL, VLDL, and other non-HDL fractions are well known to those skilled in the art.[13,19,20] For example, the precipitant can be either a high molecular weight polyanion or a combination of a polyanion and a divalent cation.

Examples of polyanions include, but are not limited to, sulfated polysaccharides, e.g., heparin, dextran sulfate; and phosphotungstic acid.

Examples of divalent cations include, but are not limited to, $Mg^{++}$, $Ca^{++}$, and $Mn^{++}$.

Examples of high molecular weight polyanions include, but are not limited to, corn amylopectin sulfate and dextran sulfate having a molecular weight greater than about 20 million.

BRIEF DESCRIPTION OF THE DRAWINGS

FIG. IA depicts a densitometric tracing of the lipoprotein electrophoretic pattern of the supernatant obtained in Example 40 after treating a highly lipemic serum sample with a prior art non-HDL precipitant A.

FIG. IB depicts a densitometric tracing of the lipoprotein electrophoretic pattern of the supernatant obtained in Example 40 after treating a highly lipemic serum sample with a non-HDL precipitant B within the scope of the instant invention.

Figure 1:
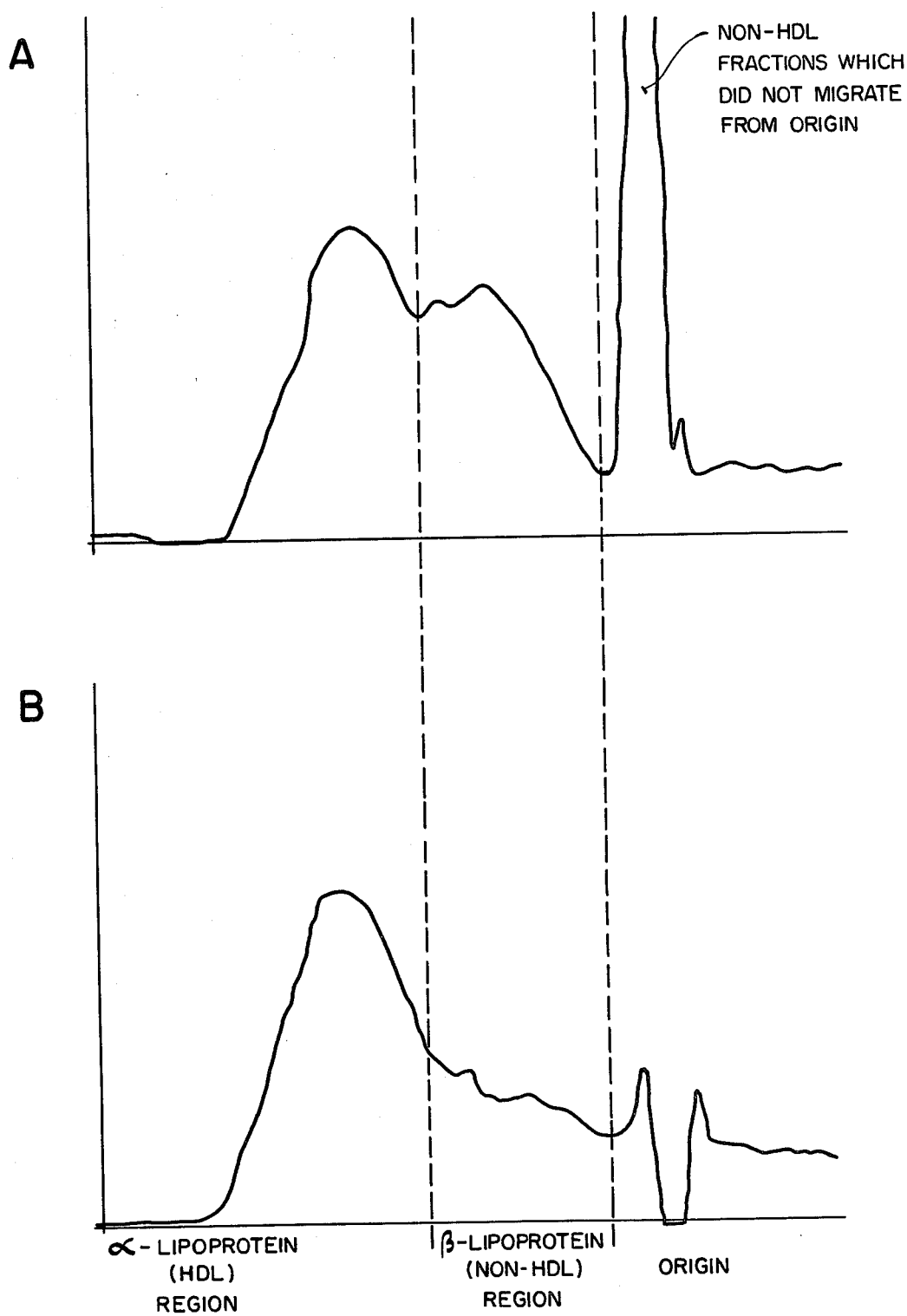
Figure 2:
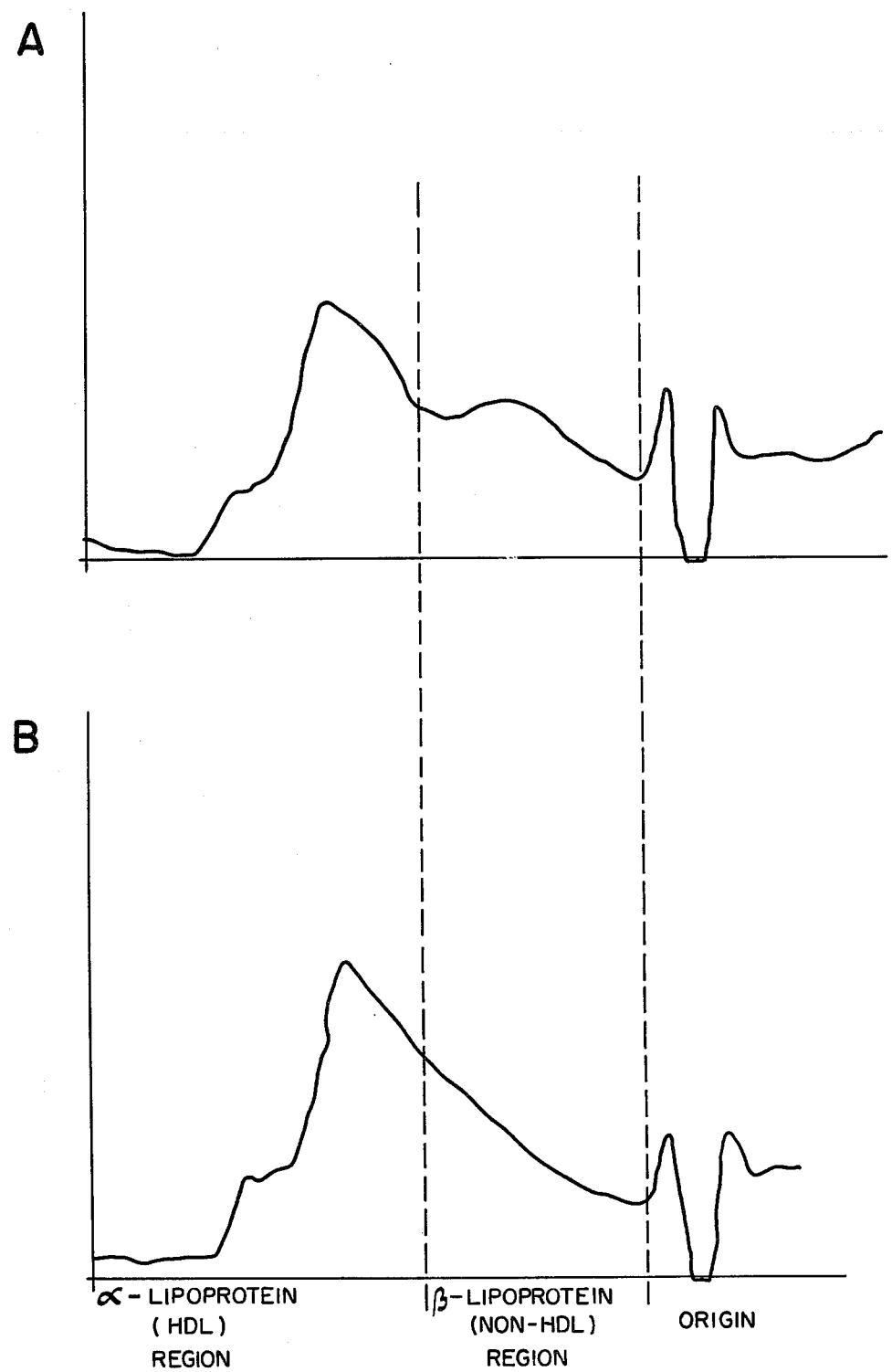

FIG. IIA depicts a densitometric tracing of the lipoprotein electrophoretic pattern of the supernatant obtained in Example 41 after treating a highly lipemic serum sample with a prior art non-HDL precipitant A.

FIG. IIB depicts a densitometric tracing of the lipoprotein electrophoretic pattern of the supernatant obtained in Example 42 after treating a highly lipemic serum sample with a non-HDL precipitant B within the scope of the instant invention.

DESCRIPTION OF THE PREFERRED EMBODIMENTS

To be suitable for use in the reagent of the instant invention, the agent must be able to pass the following two tests. The first test is designed to determine whether an agent interferes with the analysis of HDL cholesterol in a non-highly lipemic serum sample. This test can comprise mixing 40 mg of the agent to be tested with 100λ of a precipitant solution comprising 100μ moles magnesium acetate and 1 mg dextran sulfate to thereby form a test non-HDL precipitant. This test non-HDL precipitant should then be mixed with 1.0 ml of non-highly lipemic serum.

As a control, mix 100λ of a control non-HDL precipitant comprising 100μ moles magnesium acetate and 1 mg dextran sulfate with a 1.0 ml aliquot of the same serum sample present in a separate test table.

These test tubes can be analyzed for HDL cholesterol by the same procedure as employed in Examples 9–33, infra. In addition, the HDL cholesterol assays can be performed by any recognized serum cholesterol assay known to those skilled in the art.

If the HDL cholesterol value obtained using the test non-HDL precipitant differs from the HDL cholesterol value obtained using the control non-HDL precipitant by more than ±10%, it can be concluded that the agent being tested interferes with the analysis of HDL cholesterol and therefore not suitable for use in the non-HDL precipitant of the instant invention.

If the HDL cholesterol values obtained from the above procedure are within ±10% of each other, it can be concluded that the agent being tested does not interfere with the analysis of HDL cholesterol. However, one must perform a similar assay on highly lipemic serum using the same test non-HDL precipitant and a second control non-HDL precipitant comprising 100μ moles magnesium acetate, 1 mg dextran sulfate, and 40 mg of talc prior to conclusively determining whether the non-interfering agent being tested can be used in the non-HDL precipitant of the instant invention.

If the HDL cholesterol value obtained using the test non-HDL precipitant differs from the HDL cholesterol value obtained using the second control non-HDL precipitant by more than +10%, it can be concluded that the non-interfering agent being tested is not suitable for use in the non-HDL precipitants of the instant invention.

However, if the HDL cholesterol value obtained using the test non-HDL precipitant differs from the HDL cholesterol value obtained using the second control non-HDL precipitant by less than or equal to +10%, the non-interfering agent being tested enhances the flocculation of the precipitant formed by the precipitator and the various non-HDL fractions in highly lipemic serum and therefore can be used in the non-HDL precipitant of the instant invention.

It has been found that the agents which enhance the flocculation of the precipitant formed by the precipitator and the various non-HDL fractions in highly lipemic serum tend to be inert, insoluble, and adsorbtive compositions, although these properties are not deemed essential so long as the agents are non-interfering. Examples of such non-interfering agents which enhance the flocculation of the precipitant formed by the precipitator and the various non-HDL fractions in highly lipemic serum include silicic acid; kaolin; calcined alumina; activated charcoal; and powdered glass. Preferably talc, kaolin, and mixtures thereof are employed in the reagent of the present invention.

It should be understood that the term "flocculation" as used herein is not limited to its exact technical definition but denotes any process, such as sedimentation, flocculation, agglomeration, and the like whereby the separation of the precipitant formed by the precipitator and the various non-HDL fractions in highly lipemic serum is enhanced.

The reagent of the instant invention can be prepared as a solid-liquid suspension, a powdered reagent, a granular reagent or a reagent in tablet form. Methods of making solid-liquid suspensions, powdered reagents, granular reagents, and reagents in tablet form are well known to those skilled in the art. For example, methods for making reagents in tablet form are disclosed in Remington's Pharmaceutical Sciences, Mack Publishing Co., PA (1965), said publication being incorporated herein in toto by reference.

The following examples are provided for the purpose of further illustration only and are not intended to be limitations on the disclosed invention.

EXAMPLES 1–8

One non-HDL precipitant (A) within the scope of the prior art and seven non-HDL precipitants (B–H) within the scope of the instant invention were prepared. The compositions of the non-HDL precipitants were such that when mixed in 1 ml of a fluid, such as serum, would give the concentrations set forth in Table I.

TABLE I

| | NON-HDL PRECIPITANTS | | | | | | | |
|---|---|---|---|---|---|---|---|---|
| | Prior Art | Precipitants within Scope of Invention | | | | | | |
| Constituent | A[1] | B[1] | C[2] | D[1] | E[1] | F[1] | G[1] | H[1] |
| Magnesium Acetate, M | 0.1 | 0.1 | 0.1 | 0.1 | 0.1 | 0.1 | 0.1 | 0.1 |
| Dextran Sulfate, % | 0.1 | 0.1 | 0.1 | 0.1 | 0.1 | 0.1 | 0.1 | 0.1 |
| Talc, mg/ml | — | 40 | 40 | — | — | — | — | — |
| Kaolin, mg/ml | — | — | — | 40 | — | — | — | — |
| Calcined alumina, mg/ml | — | — | — | — | 40 | — | — | — |
| Silicic acid, mg/ml | — | — | — | — | — | 40 | — | — |

TABLE I-continued

NON-HDL PRECIPITANTS

| Constituent | Prior Art A[1] | Precipitants within Scope of Invention B[1] | C[2] | D[1] | E[1] | F[1] | G[1] | H[1] |
|---|---|---|---|---|---|---|---|---|
| Activated charcoal, mg/ml | — | — | — | — | — | — | 40 | — |
| Powdered glass, mg/ml | — | — | — | — | — | — | — | 40 |

[1]Liquid-solid suspension
[2]Powder reagent

EXAMPLES 9–33

Each of 25 non-highly lipemic serum samples were assayed in triplicate for HDL cholesterol according to the following procedure.

Non-HDL precipitants A, B, and C of Table I were added to individual test tubes containing 1 ml aliquots of each serum sample to be assayed. Each resulting mixture was thoroughly mixed and then allowed to stand at room temperature for 10 minutes.

All test tubes were centrifuged at high speed on a clinical centrifuge for 10 minutes.

Into individual well-matched cuvettes containing 1.0 ml of cholesterol reagent were pipetted 50 μl of each supernatant obtained from the previous step. The resulting solution was mixed well.

A blank standard was prepared in the same manner using 50 μl of reagent grade water for the blank.

All cuvettes were then incubated at 37° C. for 10 minutes.

Using the blank standard, the spectrophorometer was set to read zero absorbance at 500 nm. The absorbance of each of the well mixed supernatant-cholesterol reagent solutions were then read.

The HDL cholesterol concentrations were calculated as follows:

$$HDL\ Cholesterol\ (mg/dl) = \frac{A}{Absorptivity} \times \frac{2 \times MW}{1000} \times \frac{V_t}{V_s} \times 100 \times F$$

wherein: A = Absorbance reading of cuvette containing sample

MW = Molecular weight of cholesterol = 386.6 Two moles of cholesterol are required to produce one mole of quinoneimine, hence 2×MW $V_t$ = Total reaction volume = 1.05 ml $V_s$ = Sample Volume = 0.05 ml (50 μl)

Absorptivity = millimolar absorptivity of quinoneimine under the conditions of this assay = 13.78

F = Dilution factor = 1.01 (In precipitation step, 1.0 of serum was added to 100 μl of precipitant)

HDL cholesterol (mg/dl)

$$= \frac{A}{13.78} \times \frac{2 \times 386.6}{1000} \times \frac{1.05}{0.05} \times 100 \times 1.01$$

HDL Cholesterol (mg/dl) = A × 119

The data obtained from these assays is set forth in Table II.

TABLE II

HDL CHOLESTEROL VALUES NON-HIGHLY LIPEMIC SERUM

| | NON-HDL PRECIPITANT | | |
|---|---|---|---|
| Example No. | Prior Art A | Within Scope of Invention B | C |
| 9 | 24.4 | 23.8 | N.D. |
| 10 | 53.0 | 54.2 | N.D. |
| 11 | 34.2 | 34.0 | N.D. |
| 12 | 40.1 | 39.4 | N.D. |
| 13 | 8.9 | 9.0 | N.D. |
| 14 | 21.3 | 21.0 | 19.9 |
| 15 | 49.6 | 49.0 | 49.6 |
| 16 | 32.5 | 32.5 | 32.8 |
| 17 | 35.7 | 36.0 | 37.5 |
| 18 | 21.5 | 21.7 | 22.5 |
| 19 | 22.9 | 22.0 | 24.3 |
| 20 | 67.3 | 67.3 | 67.2 |
| 21 | 33.5 | 33.7 | 32.6 |
| 22 | 25.8 | 22.5 | 26.7 |
| 23 | 17.6 | 18.3 | 18.4 |
| 24 | 46.2 | 46.1 | 44.8 |
| 25 | 31.5 | 30.9 | 31.2 |
| 26 | 62.3 | 60.0 | 63.0 |
| 27 | 28.9 | 29.3 | 30.6 |
| 28 | 37.8 | 38.2 | 38.2 |
| 29 | 33.6 | 32.9 | 33.2 |
| 30 | 65.4 | 67.2 | 65.9 |
| 31 | 17.1 | 17.4 | 17.8 |
| 32 | 32.1 | 31.7 | 31.5 |
| 33 | 32.3 | 31.6 | 31.1 |

N.D. denotes not determined.

The results set forth in Table II indicate that non-HDL precipitants within the scope of this invention do not adversely affect HDL cholesterol values obtained from HDL cholesterol assays performed on non-highly lipemic serum. In addition, it was observed after the centrifugation step that serum samples which had been treated with non-HDL precipitants B and C (i.e., non-HDL precipitants within the scope of the instant invention) had precipitates present therein which were compacted better and therefore were more easily separable from the supernatant than the precipitates present in serum samples treated with non-HDL precipitant A (i.e., a non-HDL precipitant within the scope of the prior art).

EXAMPLES 34–39

Using the same assay procedure as employed in examples 9–33 in conjunction with prior art non-HDL precipitant A and non-HDL reagents within the scope of this invention, B and D, six highly lipemic serum samples were assayed in triplicate for HDL cholesterol and the data obtained therefrom are set forth in Table III.

TABLE III

HDL CHOLESTEROL VALUES HIGHLY LIPEMIC SERUM

| | NON-HDL PRECIPITANT | | |
|---|---|---|---|
| Example No. | Prior Art A | Within Scope of Invention B | D |
| 34 | 178.8 | 140.3 | 147.6 |
| 35 | 64.3 | 41.3 | 38.3 |
| 36 | 113.8 | 110.7 | 109.6 |
| 37 | 186.6 | 178.7 | 179.9 |
| 38 | 33.5 | 24.6 | 25.6 |
| 39 | 192.5 | 179.2 | 156.9 |

The results set forth in Table III show that reagents within the scope of the instant invention more effectively remove various non-HDL fractions from the supernatant of highly lipemic serum. Therefore, in assaying highly lipemic serum for HDL-cholesterol, the non-HDL precipitants within the scope of the instant invention eliminate the prior art necessity of having to either dilute the serum prior to the precipitation step or to filter the supernatant subsequent to the centrifugation step to avoid falsely elevated HDL cholesterol values such as those obtained with prior art reagent A as set forth in Table III.

EXAMPLES 40–41

Using the same assay procedure as employed in examples 9–33, save that ½ ml serum samples were assayed with ½ the amount of reagent employed in examples 9–33, two highly lipemic serum samples were assayed by one prior art non-HDL precipitant, A, and by 6 non-HDL precipitants within the scope of this invention, B and D-H. The data obtained therefrom are set forth in Table IV.

TABLE IV

| | HDL CHOLESTEROL VALUES HIGHLY LIPEMIC SERUM | | | | | | |
|---|---|---|---|---|---|---|---|
| | NON-HDL PRECIPITANT | | | | | | |
| Example | Prior Art | Within Scope of Invention | | | | | |
| No. | A | B | D | E | F | G | H |
| 40 | 65 | 31.5 | 30.6 | 30.3 | 29.6 | 31.3 | 31.5 |
| 41 | 31.1 | 20.8 | 19.2 | 21.9 | 19.8 | 22.4 | 22.4 |

The results set forth in Table IV again show that reagents within the scope of the instant invention more effectively remove various non-HDL fractions from the supernatant of highly lipemic serum.

To further demonstrate this point, the supernatants obtained after treating the highly lipemic sera of examples 40 and 41 with prior art non-HDL precipitant, A, and non-HDL precipitant, B, within the scope of the instant invention, were electrophoresed using a Beckman Brand Lipoprotein Electrophoresis Kit according to the instructions given therein for the electrophoresis of whole serum. The results obtained are set forth in FIGS. I and II.

A comparison of FIG. IA with FIG. IB shows that a significant amount of various non-HDL fractions (i.e., β-lipoprotein and other non-HDL which did not migrate from the origin) remained in the supernatant (FIG. IA) obtained by treating the highly lipemic serum of Example 40 with prior art non-HDL precipitant A. In contrast, FIG. IB shows that the same highly lipemic serum of Example 40 when treated with non-HDL precipitant B within the scope of the instant invention yields a supernatant which is substantially devoid of non-HDL fractions.

A similar comparison can be made with FIG. IIA and FIG. IIB.

Therefore, the falsely elevated HDL cholesterol values obtained in examples 40 and 41, as well as in examples 34–39, when assaying highly lipemic serum in conjunction with prior art non-HDL precipitant A is due to the fact that the prior art non-HDL precipitant does not completely remove various non-HDL fractions from the supernatant. In contrast, non-HDL precipitants within the scope of the instant invention effectively remove various non-HDL from the supernatant and thereby, in the case of very lipemic serum, eliminate the necessity of either having to dilute the serum prior to the precipitation step or of having to filter the supernatant subsequent to the centrifugation step to avoid falsely elevated HDL cholesterol values.

EXAMPLE 42

Using the same assay procedure employed in examples 9–33 in conjunction with 50 μl of a test non-HDL precipitant comprising 50μ moles magnesium acetate, 0.5 mg dextran sulfate, and 20 mg fumed silica and 50 μl of a control non-HDL precipitant comprising 50μ moles magnesium acetate and 0.5 mg dextran sulfate, 0.5 ml aliquots of a non-highly lipemic serum sample are assayed for HDL cholesterol. The data from this test would reveal that substantially all HDL cholesterol is removed from the supernatant. Therefore, fumed silica interferes with the analysis of HDL cholesterol and accordingly is not suitable for use in the non-HDL precipitants of the instant invention.

EXAMPLE 43

Using the same assay procedure employed in examples 9–33 in conjunction with 50 μl of a test non-HDL precipitant comprising 50μ moles magnesium acetate, 0.5 mg dextran sulfate, and 20 mg diatomaceous earth and 50 μl of the control non-HDL precipitant employed in Example 42, 0.5 ml aliquots of a non-highly lipemic serum sample were assayed for HDL cholesterol. The data obtained therefrom are set forth in Table V.

TABLE V

| | HDL CHOLESTEROL VALUES NON-HIGHLY LIPEMIC SERUM | |
|---|---|---|
| | Test Non-HDL Precipitant | Control Non-HDL Precipitant |
| HDL Cholesterol, mg/dl | 31.6 | 30.9 |

The data set forth in Table V indicate that the HDL cholesterol values obtained from the above procedure are within ±10% of each other. Therefore, the same assay procedure was employed using 0.5 ml aliquots of highly lipemic serum in conjunction with the same test non-HDL precipitant and 50 μl of second control non-HDL precipitant comprising 50μ moles magnesium acetate, 0.5 mg dextran sulfate, and 20 mg talc. The data obtained from this second test are set forth in Table VI.

TABLE VI

| | HDL CHOLESTEROL VALUES HIGHLY LIPEMIC SERUM | |
|---|---|---|
| | Test Non-HDL Precipitant | Second Control Non-HDL Precipitant |
| HDL | 175.0 | 140.3 |

The data set forth in Table VI indicate that the HDL cholesterol value obtained using the test non-HDL precipitant differs from the HDL cholesterol value obtained using the second control non-HDL precipitant by more than +10%. Therefore, although diatomaceous earth does not interfere in with the analysis of HDL cholesterol, diatomaceous earth does not enhance the flocculation of the precipitant formed by the precipitator and the various non-HDL fractions in highly lipemic serum. Accordingly, diatomaceous earth is not suitable for use in the non-HDL precipitants of the instant invention.

Based upon this disclosure, many other modifications and ramifications will naturally suggest themselves to those skilled in the art of serum analysis. These are intended to be comprehended within the scope of this invention.

BIBLIOGRAPHY

1. Barr et al., *Am. J. Med.*, 11: 480, (1951).
2. Barr, *Circulation*, 8: 641 (1953).
3. Berg et al., *Lancet*, 1: 499 (1976).
4. Sven et al., *Scand. J. Clin. Lab. Invest.*, 37: 251 (1977).
5. Kannel et al., Serum Cholesterol, *Ann. Intern. Med.*, b 74: 1 (1971).
6. Castelli et al., *Circulation*, 51/52: II-97(a) (1975).
7. Gordon et al., *Am. J. Med.*, 62: 707 (1977).
8. Miller et al., *Lancet*, 1: 965 (1977).
9. Rhoads et al., *N. Eng. J. Med.*, 294: 293 (1976).
10. Havel et al., *J. Clin. Invest.*, 34: 1345 (1955).
11. Jencks et al., *J. Clin. Invest.*, 35: 980 (1956).
12. Burnstein et al., *Clin. Chem. Acta*, 5: 609 (1960).
13. Burnstein et al., *J. Lipid Res.*, 11: 583 (1970).
14. Wilson et al., *J. Lab. Clin. Med.*, 82: 473 (1973).
15. Bachorik et al., *Clin. Chem.*, 22: 1828 (1976).
16. Lopes-Virella et al., *Clin. Chem.*, 23: 882 (1977).
17. Lipid and Lipoprotein Analysis in Manual of Laboratory Operations, Lipid Research Clinics Program, 1, DHEW Publication No. (NIH) 75–628, National Heart and Lung Institute, National Institutes of Health, Bethesda, Md 20014.
18. Steele et al., Clin. Chem., 22: 98 (1976).
19. Cornwell et al., *J. Lipid Res.*, 2 (2): 110 (1961).
20. Bernfield et al., *J. of Biological Chem.*, 235 (10): 2852 (1960).

The above publications are incorporated herein in toto by reference.

The embodiments of the invention in which an exclusive property or privilege is claimed are defined as follows:

1. In a reagent comprising a non-high density lipoprotein precipitator capable of precipitating low density lipoproteins, very low density lipoproteins, and other non-high density lipoproteins, the improvement wherein said reagent further comprises an inert, water-insoluble, adsorptive agent which is non-interfering with analysis of HDL cholesterol and capable of enhancing the flocculation of a precipitant formed by said precipitator and said non-high density lipoprotein fractions in highly lipemic serum.

2. The reagent of claim 1 wherein said inert, insoluble, adsorptive agent is selected from a group consisting of silicic acid; kaolin; calcined alumina; talc; activated charcoal; powdered glass; and mixtures thereof.

3. The reagent of claim 2 wherein said inert, insoluble, adsorptive agent is selected from the group consisting of talc, kaolin, and mixtures thereof.

4. The reagent of claim 3 wherein said inert, insoluble, adsorptive agent is talc.

5. The reagent of claim 1 wherein said precipitator comprises dextran sulfate and magnesium cations.

6. The reagent of claim 2 wherein said precipitator comprises dextran sulfate and magnesium cations.

7. The reagent of claim 3 wherein said precipitator comprises dextran sulfate and magnesium cations.

8. The reagent of claim 4 wherein said precipitator comprises dextran sulfate and magnesium cations.

9. A powdered reagent prepared from the reagent of claim 1.

10. A powdered reagent prepared from the reagent of claim 2.

11. A powdered reagent prepared from the reagent of claim 3.

12. A powdered reagent prepared from the reagent of claim 4.

13. A powdered reagent prepared from the reagent of claim 5.

14. A powdered reagent prepared from the reagent of claim 6.

15. A powdered reagent prepared from the reagent of claim 7.

16. A powdered reagent prepared from the reagent of claim 8.

17. A granular reagent comprising the reagent of claim 1.

18. A granular reagent comprising the reagent of claim 2.

19. A granular reagent comprising the reagent of claim 3.

20. A granular reagent comprising the reagent of claim 4.

21. A granular reagent comprising the reagent of claim 5.

22. A granular reagent comprising the reagent of claim 6.

23. A granular reagent comprising the reagent of claim 7.

24. A granular reagent comprising the reagent of claim 8.

25. A tablet comprising the reagent of claim 1.
26. A tablet comprising the reagent of claim 2.
27. A tablet comprising the reagent of claim 3.
28. A tablet comprising the reagent of claim 4.
29. A tablet comprising the reagent of claim 5.
30. A tablet comprising the reagent of claim 6.
31. A tablet comprising the reagent of claim 7.
32. A tablet comprising the reagent of claim 8.

33. The tablet of claim 25 comprising about 15 mg anhydrous magnesium acetate, about 1 mg of dextran sulfate, about 40 mg of talc, about 6 mg of derivatized starch, and about 38 mg of microcrystalline cellulose.

34. In a method of precipitating non-HDL cholesterol comprising contacting a non-HDL precipitator with a serum sample to be assayed, the improvement wherein said pre non-HDL precipitator employed therein is the reagent of claims 1 or 2 or 3 or 4 or 5 or 6 or 7 or 8 or 9 or 10 or 11 or 12 or 13 or 14 or 15 or 16 or 17 or 18 or 19 or 20 or 21 or 22 or 23 or 24 or 25 or 26 or 27 or 28 or 29 or 30 or 31 or 32 or 33.

* * * * *